(12) United States Patent
Kalló et al.

(10) Patent No.: US 6,175,641 B1
(45) Date of Patent: Jan. 16, 2001

(54) DETECTOR FOR RECOGNIZING THE LIVING CHARACTER OF A FINGER IN A FINGERPRINT RECOGNIZING APPARATUS

(75) Inventors: Péter Kalló; Imre Kiss; András Podmaniczky, all of Budapest; János Tálosi, Nagykanizsa, all of (HU)

(73) Assignee: Dermo Corporation, Ltd., Hamilton (BM)

( * ) Notice: Under 35 U.S.C. 154(b), the term of this patent shall be extended for 0 days.

(21) Appl. No.: 09/051,154

(22) PCT Filed: Oct. 4, 1996

(86) PCT No.: PCT/HU96/00056

§ 371 Date: Apr. 2, 1998

§ 102(e) Date: Apr. 2, 1998

(87) PCT Pub. No.: WO97/14111

PCT Pub. Date: Apr. 17, 1997

(30) Foreign Application Priority Data

Oct. 6, 1995 (HU) .................................................. 9502937

(51) Int. Cl.[7] .................................................. G06K 9/20
(52) U.S. Cl. .................................. 382/124; 382/116
(58) Field of Search .................................. 382/124, 312, 382/125, 318, 126, 315, 127, 116; 356/71; 340/825.34

(56) References Cited

U.S. PATENT DOCUMENTS

| | | | |
|---|---|---|---|
| 3,622,989 | * 11/1971 | Dowdy, Sr. | 382/126 |
| 3,639,905 | * 2/1972 | Yaida et al. | 430/149 |
| 3,781,855 | * 12/1973 | Killen | 382/126 |
| 4,210,899 | * 7/1980 | Swonger et al. | 340/146.3 E |
| 4,353,056 | * 10/1982 | Tsikos | 340/146.3 E |
| 4,784,484 | * 11/1988 | Jensen | 356/71 |
| 5,077,803 | * 12/1991 | Kato et al. | 382/4 |
| 5,095,278 | * 3/1992 | Hendrick | 324/687 |
| 5,419,826 | * 5/1995 | Zirino | 204/416 |
| 5,623,552 | * 4/1997 | Lane | 382/124 |
| 5,629,764 | * 5/1997 | Bahuguna et al. | 356/71 |
| 5,635,723 | * 6/1997 | Fujieda et al. | 250/556 |

FOREIGN PATENT DOCUMENTS

| | | | |
|---|---|---|---|
| 0488116A2 | * 6/1992 | (EP) | C09K/19/00 |
| 1-180685A | * 1/1990 | (JP) | G06K/9/00 |
| 402001243A | * 6/1992 | (JP) | A61B/5/117 |

* cited by examiner

Primary Examiner—Leo H. Boudreau
Assistant Examiner—Brian P. Werner
(74) Attorney, Agent, or Firm—Finnegan, Henderson, Farabow, Garrett and Dunner, L.L.P.

(57) ABSTRACT

Detector for recognizing the living character of a finger which is arranged in a fingerprint recognizing apparatus and the detector is in contact with a print area (2) of the living finger constituting a print forming element (1) and the apparatus comprises for the examination of the print area (2) a print detector (5) which has a print imaging surface (4) partially covered by the print area (2). The detector comprises an electrode system (3) made of an electrically conductive material and sensing the presence of the print forming element (1), and an electrical evaluation unit coupled through electrical contacts (10) to the electrode system (3), the unit senses the change in state in the electrode system (3) caused by the proximity of the print forming element (1). The electrode system (3) is arranged on a portion of the print detector (5) covered by the print area (2) and it is coupled to the print imaging surface (4).

13 Claims, 3 Drawing Sheets

DETECTOR FOR RECOGNIZING THE LIVING CHARACTER OF A FINGER IN A FINGERPRINT RECOGNIZING APPARATUS

This is a national stage (371) filing of PCT/HU96/00056, filed on Oct. 4, 1996, and published as WO 97/14111 on Apr. 17, 1997.

BACKGROUND OF THE INVENTION

1. Field of the Invention

The invention relates to a detector for recognizing the living character of a finger that is arranged in a fingerprint recognizing apparatus. The detector is in contact with a print area of the living finger that constitutes a print forming element, and for the examination of the print area the apparatus comprises a print detector that has a print imaging surface partially covered by the print area, and the detector comprises an electrode system made of an electrically conductive material that senses the presence of the print forming element. The detector further comprises an electrical evaluation unit coupled through electrical contacts to the electrode system, the unit senses the change in state in the electrode system caused by the proximity of the print forming element.

2. Background of the Related Art

The identification of individuals on the basis of fingerprint recognition has become recently a widely used technique. In case of conventional fingerprint analysis using a painted paper as well as in case of opto-electric fingerprint recognition systems the fingerprints are obtained when the tip of a finger is pressed against a surface. The modern opto-electric fingerprint recognition can take place under human supervision (e.g., when the fingerprint is entered in the criminal record) or without any supervision (e.g., in case of access control systems).

In case of fingerprint recognition without human supervision the fingerprint reading apparatus can be deceived by using a plastic imprint copy made from the finger of the person to be identified, thus a false access cannot be excluded. Therefore, in protection or security systems as well as in systems permitting access to computer systems and in any other similar application, in addition to the fingerprint recognition, determining whether the print has been taken from a living finger or from a copy is of vital importance. Moreover, the process of detecting the living character of the finger in a fast and reliable manner is also an important objective.

There are known methods for detecting the living character of a finger. In the EP 0194783 A2 the optical spectral reflection coefficient of the finger is measured at two wavelengths. The measurement of the reflection coefficient takes place at the two free sides of the finger pressed to the fingerprint recognizing apparatus. The quotient of the two reflection coefficients varies during the placement of the finger to the print area from a position where the tip of the finger just touches the surface till the fully pressed state. The detection of the living character of the finger is based on the detected changes of the quotient of the reflection coefficient. The drawback of this technique lies in that if a thin, transparent copy made by a thin film is placed on a living finger of another person, the change of the quotient of the reflection coefficient will be characteristic to a living finger, and a false detection is obtained. Such a system is used in the personal identification apparatus manufactured by the company Biometrics Technology as reported in "The Biometrics Report, ISBN 190018009, 1995. page 69".

In the Japanese patent publication 053309082 an example can be found wherein the measurements are based on the electrical resistance as one property of the print forming element. In this technique an electrode is provided that contacts the surface of the finger just below the first joint, i.e., which is outside the area from where the fingerprint is taken. The electrode is used to detect the electrical resistance of the living finger. The resistance value depends on the humidity of the finger, and if this resistance falls in a predetermined range, the living character will be established. This identification is not reliable either, since the detection takes place at a location which differs from the location from where the fingerprint is taken. If a thin copy is placed between the finger tip and a print area, the contacts can still engage the living finger.

FIG. 34 of the EP 0 359 554 A2 shows an electrical system which also utilizes the difference in the resistance value of a living finger and of a replica, wherein the area used for determining the resistance value falls in the field from where the fingerprint is taken. The cited publication describes this technical solution as one where the electrode patterns used for determining the resistance value may disturb the image of the fingerprint. Furthermore, it has been analyzed that in such a system the allowable resistance value must be very large, however, then the difference between the resistance value of the finger and the replica will become smaller thus the security of such a system can be insufficient.

It can be understood from the above described known methods that they are inappropriate for reliably detecting whether the living finger belongs to the authorized person or not.

SUMMARY OF THE INVENTION

The advantages and purposes of the invention will be set forth in part in the description which follows, and in part will be obvious from the description, or may be learned by practice of the invention. Moreover, the advantages and purposes of the invention will be realized and attained by means of the elements and combinations particularly pointed out in the appended claims.

The object of the invention is to provide a detection system that can detect the living character of a finger, is associated with a fingerprint recognizing apparatus, and can prevent false identification if the person is different from the one whose fingerprint serves as a basis for recognition.

This object can be achieved by a detection system, wherein the recognition of the living character of a finger is determined by the evaluation of the electrical signals of in electrode system arranged within the print area of a print area surface, and it takes place simultaneously with the recognition of the fingerprint, wherein the electrode system is designed in such a way that the two simultaneous measurements cannot disturb one another.

An electrode system designed according to the invention not only does not disturb or limit the fingerprint recognition process, but also enables the measurement of one or more properties or the changes of these properties of a living finger at the same time as the recognition of the fingerprint takes place. Such properties can be, for example:

electrical properties (e.g., dielectric constant, impedance, etc.);

biophysical properties (e.g., points of acupuncture, reflex points, etc.); or biochemical properties (e.g., pH surface humidity, etc.).

An increased reliability can be provided by combining several kinds of detection, e.g., by using measurements taken from different surface areas and/or using an electrode system with combined patterns and/or measuring one or more properties or the variation of these properties, wherein multiple conditions can be defined for the determination of the living character of the finger.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention. In the drawings.

DETAILED DESCRIPTION

Figure 1:
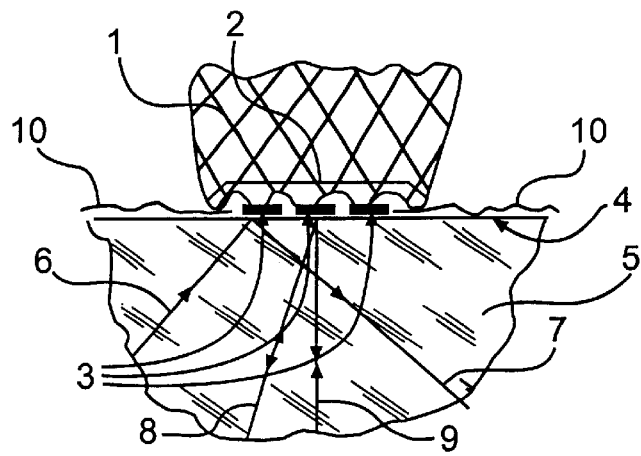
FIG. 1 shows the basic arrangement of a, detector usable for simultaneous detection of the living character of a finger and of the fingerprint itself.

Reference will now be made in detail to the present preferred embodiments of the invention illustrated in the accompanying drawings. Wherever possible, the same reference numbers are used throughout the drawings to refer to the same or like parts.

The basic operational principles of the detector for recognizing the living character of a finger will now be described in connection with FIG. 1. As shown, a print forming element 1, e.g., a living finger, gets in contact with electrode system 3 of a detector along a print area 2 when pressed to the surface of the detector. The electrode system 3 is arranged on a print imaging surface 4 designed preferably as a planar surface of a print detector 5.

The material of the print detector 5 is preferably optical glass or a transparent plastic material. When the fingerprint is imaged by means of opto-electrical imaging, the image of the fingerprint will be created primarily on the print imaging surface 4, and this image will be converted into an electrical signal sequence by means or a two-dimensional detector system (e.g., preferably a CCD detector). When the imaging takes place by means of a total reflection method, illuminating light beams 6 and image forming light beams 7 are used. When the image forming is based on light diffraction, at least one free path should be provided to illuminating light beams 8 and image forming (e.g., back-scattered) light beams 9. The role of these light beams 8 and 9 can be interchanged.

In FIG. 1 the electrode system 3 together with lead out contacts are designed as a thin layer electrode. The lead out contacts form additional parts of the electrode. The material of the electrode has a good electrical conductivity and preferably is transparent at the wavelengths of the illuminating light beams 6 or 8. Respective electrical connections are coupled to the lead out contacts. The electrical connections can be made by, for example, metal wires. The wires can be contacted in any reliable manner, e.g., by means of an ultrasonic thermal binding to the thin layer, by electrically conductive paints, or by means of an epoxy-based adhesive filled with a plurality of tiny gold particles.

The literature describes several examples for making thin layers which are electrically conductive and at the same time light transparent. Such technologies include, for example, the use of chemicals, vacuum sputtering, vacuum evaporation or plasma techniques, and the structure of the electrode system 3 can be made by the conventional use of masks. The material of the layer can be, for example, the mixture of indium-dioxide ($In_2O_3$) and tin-oxide ($Sn_2O$) referred often to as ITO layer. Further layers like pure tin-oxide layers and mixtures including aluminum-zinc-oxides ($Al_2,ZnO_2$) are also used. Such layers are not only electrically conductive and light transparent but they have the required resistance against mechanical and thermal loads. The typical thickness of thin layers falls in the range of 20 to 100 $\mu$m and their specific electrical resistance is in the range of $R\square=250$ to 1000 ohm/$\square$ they have a sufficiently high light transparency (e.g., practically close to 95%). When such layers are used, the full print area 2 can be imaged, since the presence of the thin layer cannot change the contrast of the detected image in any of the cited image detection methods using either total reflection or light diffraction. The contrast of the image of the fingerprint is typically 50–80% and relative to this amount the additional contrast modulation of 5% caused by the presence of the transparent thin layer is negligibly small.

The electrode system 3 of the detector can also be realized by using a thin layer that is either not light transparent or has only a limited transparency. Such thin layers includes, for example, thin metal layers made typically by gold, aluminum, chrome and similar metals. Such less light transparent layers are cheaper, however, their significant drawback lies in that the print surface sections covered by their structure cannot be imaged, thus such sections cannot take part in the identification of the fingerprint.

Figure 2:
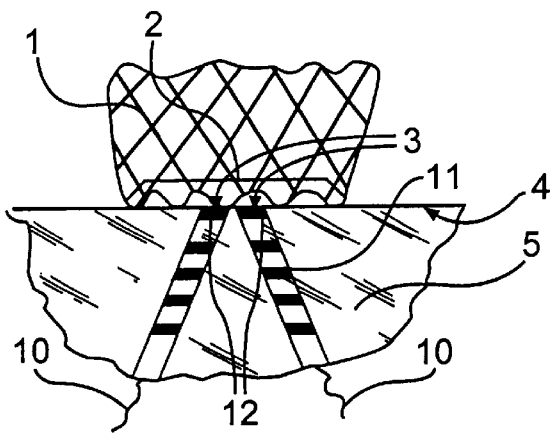
FIG. 2 shows an embodiment of an electrode systems which has a design other than using thin layers, wherein the electric connections can be seen.

FIG. 2 shows an embodiment of the electrode system 31 together with electrical contacts 10 made without using the thin layer technique. In this embodiment, the pattern of the electrode system 31 is constituted by the fiber ends 12 of electrically conductive wires 11 embedded in the material of the print detector 5. The conductive wires 11 constitute at the same time the lead out wires. The electricity conductive wires 11 can be made either by thin metal wires or by glass fibers doped by metal ions. In the last mentioned alternative, the additional advantages of light transparency will be obtained. In connection with FIG. 2, it should be noted that when the print imaging surface 4 is made (e.g., by means of grinding or polishing) the electrode system 3 constituted by the fiber ends 12 will form part of the print imaging surface 4.

Figure 3:
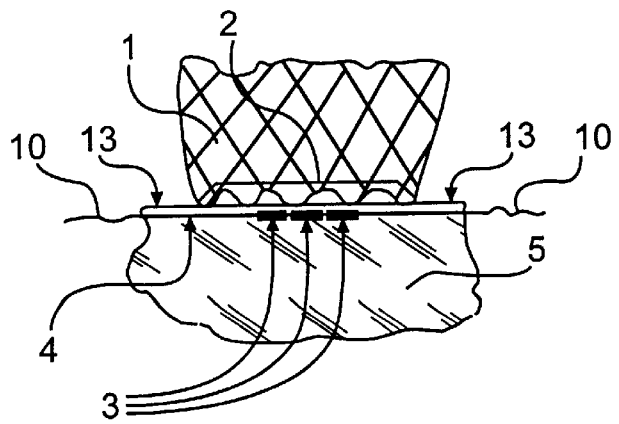
FIG. 3 shows an electrode system covered partially with an insulating thin layer.

In the embodiment shown in FIG. 3, the print forming element 1 is partially or completely insulated from the electrode system 3 by means of an intermediate electrically insulating thin layer 13, and the degree of insulation depends on the material property to be determined. If the insulating thin layer 13 completely covers the electrode system 3, the print forming element 1 will reach the close proximity of the electrode system 3. The close proximity means that the print forming element 1 will be in the electric field of the electrode system 3. In case of thin layers the corresponding distance is not more than a few micrometers, and the penetration is apparent. The required limit of proximity depends on the pattern of the electrode system, and in case of predetermined patterns several times 100 $\mu$m can be sufficient. The electrically insulating electrode system 3 is an important requirement when the measured material property is constituted by the dielectric constant.

The preparation of thin insulating layers is known from the state of art. Such layers are made typically by silicon-dioxide by vacuum deposition technique.

Figure 4:
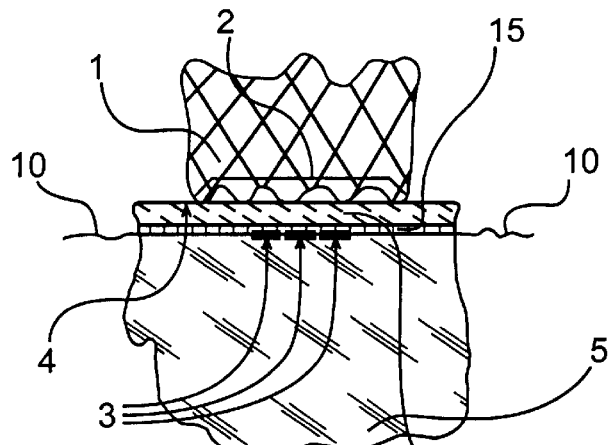
FIG. 4 shows an electrode system covered by a glass plate.

FIG. 4 shows a further embodiment for electrically insulating the electrode system 3. The print imaging surface that carries the electrode system 3 is covered by an insulating cover sheet 14 in such a way that the sheet is coupled to the print imaging surface 4 by means of an optical adhesive. Such optical adhesive materials are known in the art and they are transparent and have optical refraction indices close to that of glass, therefore they cannot cause undesired light reflections, i.e., a correct optical coupling is provided thereby. The presence of such a light transparent covering layer 15 will not prevent the illuminating light beams 6 and 8 from reaching the print detector 5 and from imaging the fingerprint. Obviously, in that case the role of the print imaging surface 4 will be played by the surface of the electrically insulating cover sheet 14 that contacts the print forming element 1.

Figure 5:
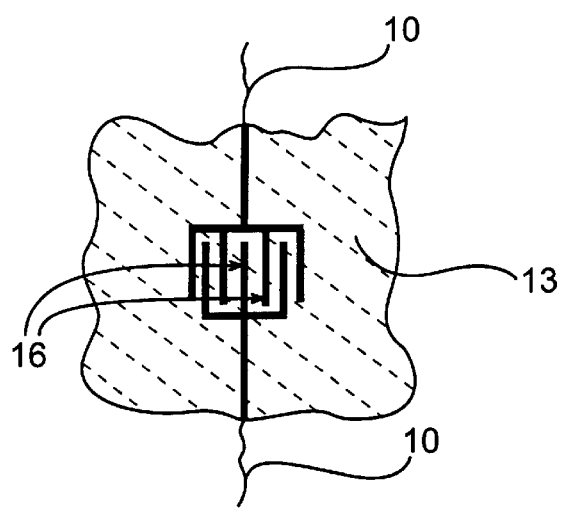
FIG. 5 shows an embodiment of a pattern of a single element electrode system used preferably for measuring the dielectric constant.

FIG. 5 shows the patterns of an element of the electrode system 3 used for measuring the dielectric constant. The pattern together with the lead out conductors is completely insulated from the print forming element 1 along the full surface of the electrically insulating thin layer 13. The pattern itself is a version of a so-called interdigital electrode 16 optimized for measuring the dielectric constant. The interdigital electrode 16 comprises a pair of oppositely arranged "comb" patterns. Such an electrode type is known for uses with respect to other objectives and principles in different fields of endeavor, e.g., in the field of acoustic filters with surface waves. The typical size data of the electrode pattern used for measuring dielectric constant are: the line width of the comb lies between 5–100 $\mu$m and the spacing between the lines is between 5–100 $\mu$m. By means of the interdigital electrode 16, it is possible to determine the dependence of the dielectric constant from the frequency. The size data of the pattern of the comb can vary according to the frequency range used. In practice, the examining frequency range is between 0.1 and 200 kHz. In this frequency range, the dielectric constant of living tissues largely differ from that of commercially available plastics (Hedvig P.: Applied Polymer Analysis and Characterization, Vol. II, Chapter 5., Hauser Publisher, Munich, 1992). The typical relative dielectric constant value of living body tissues is between about 60 and 90, while in case of plastics this value is between about 5 and 30. The difference is sufficiently large for the distinction of living tissues from plastics.

Figure 6:
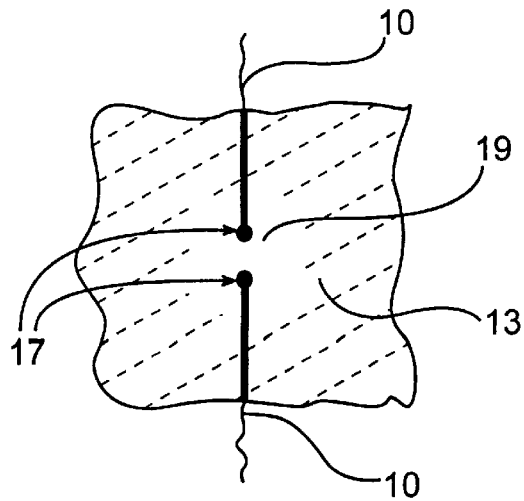
FIG. 6 shows a further pattern of a single element electrode system used preferably for measuring the electrical impedance of the print forming element.

FIG. 6 shows the pattern of an element of the electrode system 3 used for determining the electrical impedance. The pattern represents the so-called double dot electrode 17 as optimized for electrical impedance measurements. The typical size of the sensor dots is between about 0.1 and 1 mm, and the spacing between the dots is 1 to 5 mm. The dots of the measurement dot electrode 17 are in electrical contact with print forming element 1, because respective open windows 19 are made at the dot locations on the insulating thin layer 13 that covers the pattern, while the lead out conductors of the dots are electrically insulated from the print forming element 1.

Figure 7:
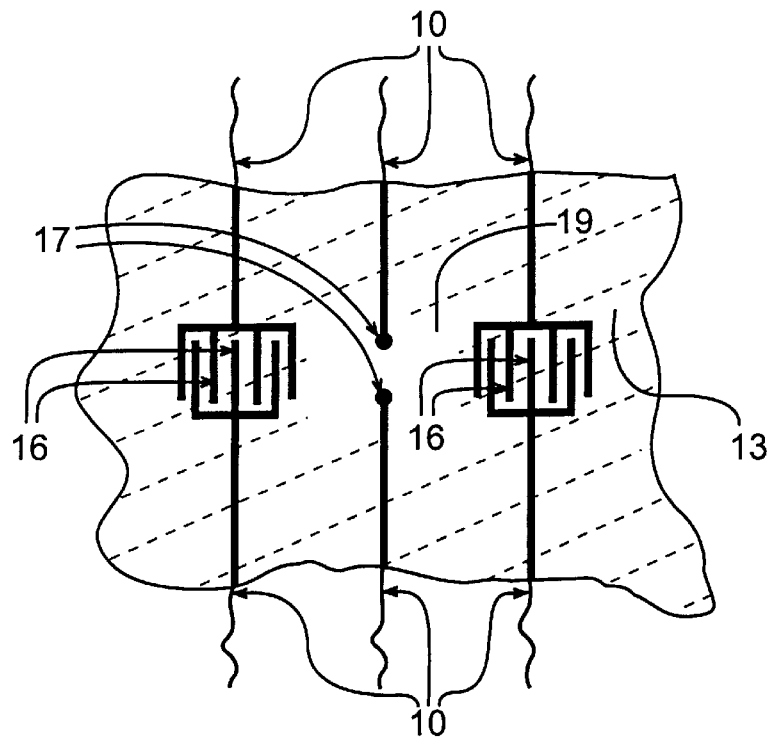
FIG. 7 shows the pattern of an electrode system with three elements used preferably for the simultaneous measurement of dielectric constant and electrical impedance.

FIG. 7 shows an electrode system 3 comprising three elements. Two of the elements constitute respective interdigital electrodes 16 while the third one is a double dot electrode 17. The size of the patterns of the two interdigital electrode elements can be varied depending on the frequency range of the dielectric constant measurement. The use of multiple frequency ranges further increases the reliability of identifying living fingers. On the electrically insulating thin layer 13 that covers the electrode system 3 a window 19 is provided for enabling impedance measurement as shown in FIG. 6.

Figure 8:
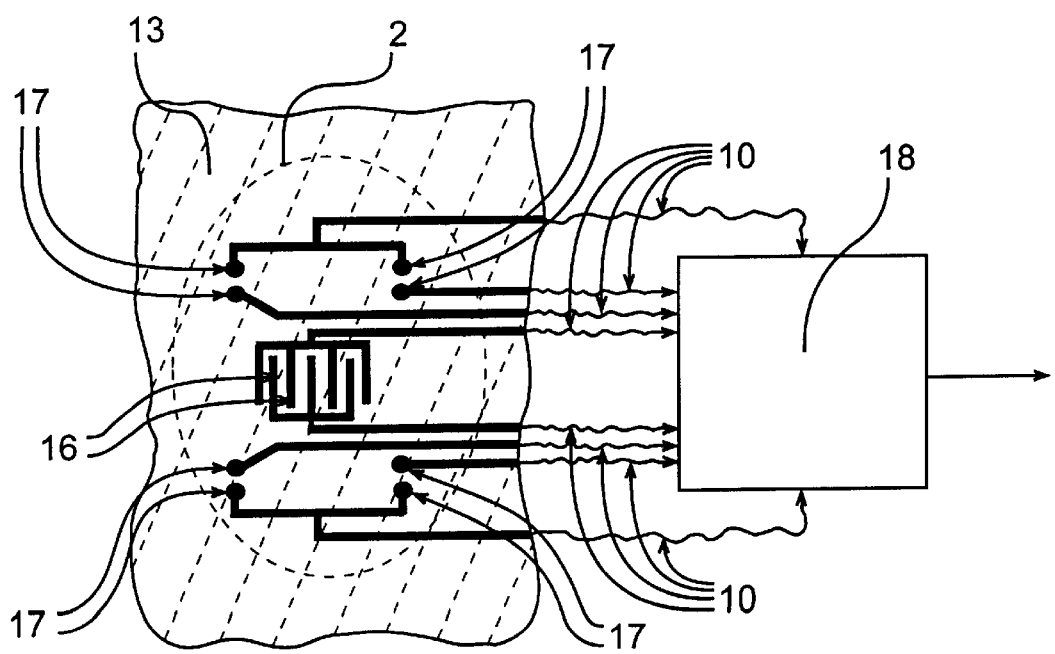
FIG. 8 shows a multiple element electrode system and its pattern made from an electrically conductive and light transparent material for the measurement of dielectric constant and electrical impedance.

FIG. 8 shows a preferable embodiment of the detector according to the invention that uses multiple element electrode system 3. The double dot electrode elements of the electrode system 3 are arranged within the print area 2 about 3 to 5 mm from the contour line, while the interdigital electrode element 16 is arranged in the central portion of the print area. In this exemplary arrangement, the print area 2 is sufficiently covered by a number of elements of the electrode system, and it prevent a false copy, which covers only a portion of the print area, from causing an erroneous personal identification. Naturally, the number of elements in the electrode system 3 can be increased and several other patterns and arrangements can be made within the scope of the present invention.

The electrical contacts 10 of the elements of the electrode system 33 are connected to the inputs of an electrical evaluating unit 18. This unit 18 can determine 10 not only the static values of certain material properties of the print forming element 1, but also determine the variation of such material properties as a function of time. The measuring of such changes should be carried out preferably during the time between the print forming element 1 touches the print imaging surface 4 until it will be pressed thereto. The typical value of this time is between about 0.2 and 0.6 sec.

The electrical evaluation unit 18 generates an enable signal for the fingerprint identification or it provides data for the central processor unit of the fingerprint identifying apparatus and this unit enables appropriate identification by analyzing the data obtained. Such an electric evaluation unit can be designed in several ways as it is obvious to those familiar with the measurement technique using micro controllers.

Other embodiments of the invention will be apparent to those skilled in the art from consideration of the specification and practice of the invention disclosed herein. It is intended that the specification and examples be considered as exemplary only. Thus it should be understood that the invention is not limited to the illustrative examples in this specification. Rather, the invention is intended to cover all modifications and variations that come within the scope of the following claims and their equivalents.

What is claimed is:

1. A detector for recognizing the living character of a finger in an opto-electronic fingerprint recognizing apparatus, in which a full two-dimensional image of the fingerprint is captured, and in operation the detector is in contact with a print area of a living finger constituting a print forming element, the fingerprint recognizing apparatus comprises a print detector for examining said print area, the print detector having a print imaging surface partially covered by said print area, the detector comprising:
- an electrode system made of an electrically conductive material, and arranged on a portion of said print detector covered by said print area, and being coupled to said print imaging surface;
- an electrical evaluation unit coupled through electrical contacts to the electrode system, said electrical evaluation unit sensing a change in state of the electrode system caused by the proximity of the print forming element;
- wherein said electrode system comprises interdigital electrodes covered completely by a non-conductive layer; and
- wherein said print imaging surface is constituted by said electrically non-conductive and light transparent material comprised of a thin separate layer deposited on the print detector so as to cover at least a dominant portion of said print area, said electrode system and said electrical contacts, and said electrode system and said electrical contacts are made of light transparent and electrically conductive material configured to allow print images to be captured of the print forming element on at least one portion of the print area covered by said electrode system and said electrical contacts, and said electrode system is designed for determining dielectric constant.

2. The detector as claimed in claim 1, wherein said electrode system simultaneously determines the dielectric constant of the print forming element while the print image of the print forming element is captured.

3. A detector for recognizing the living character of a finger in an opto-electronic fingerprint recognizing apparatus, in which a full two-dimensional image of the fingerprint is captured, and in operation the detector is in contact with a print area of a living finger constituting a print forming element, the fingerprint recognizing apparatus comprises a print detector for examining said print area, the print detector having a print imaging surface partially covered by said print area, the detector comprising:
- an electrode system made of an electrically conductive material, and arranged on a portion of said print detector covered by said print area, and being coupled to said print imaging surface;
- an electrical evaluation unit coupled through electrical contacts to the electrode system, said electrical evaluation unit sensing a change in state of the electrode system caused by the proximity of the print forming element;
- wherein said electrode system comprises at least one double dot electrode;
- wherein said print imaging surface is constituted by an electrically non-conductive and light transparent material comprised of a thin separate layer deposited on the print detector so as to cover at least a dominant portion of said print area, said electrode system and said electrical contacts, and said electrode system and said electrical contacts are made of light transparent and electrical conductive material configured to allow print images to be captured of the print forming element on at least one portion of the print area covered by said electrode system and said electrical contacts, and
- wherein said electrode system is designed for determining electrical impedance, and said electrically non-conductive layer leaves said double dot electrode and a close vicinity thereof uncovered while covering lead out contacts of the electrode system.

4. The detector as claimed in claim 3, wherein said electrode system simultaneously determines electrical impedance of the print forming element while the print image of the print forming element is captured.

5. A detector for recognizing the living character of a finger in an opto-electronic fingerprint recognizing apparatus, in which a full two-dimensional image of the fingerprint is captured, and in operation the detector is in contact with a print area of a living finger constituting a print forming element, the fingerprint recognizing apparatus comprises a print detector for examining said print area, the print detector having a print imaging surface partially covered by said print area, the detector comprising:
- an electrode system made of an electrically conductive material, and arranged on a portion of said print detector covered by said print area, and being coupled to said print imaging surface;
- an electrical evaluation unit coupled through electrical contacts to the electrode system, said electrical evaluation unit sensing a change in state of the electrode system caused by the proximity of the print forming element;
- wherein said electrode system comprises at least one double dot electrode;
- wherein said print imaging surface is constituted by an electrically non-conductive and light transparent material comprised of a thin separate layer deposited on the print detector so as to cover at least a dominant portion of said print area, said electrode system and said electrical contacts, and said electrode system and said electrical contacts are made of light transparent and electrically conductive material configured to allow print images to be captured of the print forming element on at least one portion of the print area covered by said electrode system and said electrical contacts, and the electrode system comprises fiber ends of electrically conductive wires embedded in the non-conductive material of said print detector and said fiber ends forming part of said print imaging surface, wherein the remaining portion of said print imaging surface constitutes said non-conductive portion.

6. The detector as claimed in claim 5, wherein said electrically conductive wires are comprised of thin wires or glass fibers doped by metal ions configured so that said electrically conductive wires do not interfere with capturing the full two-dimensional image of the fingerprint.

7. An optical-electronic print recognizing device for capturing print images of a print forming element comprising:
- a print detector structure made of an electrically insulating and light transparent material and defining a print area for receiving a print forming element;
- an electrode system coupled to said print detector structure for generating a change in state when the print forming element is proximate to at least one portion of the print area covered by the electrode system;
- an electrical evaluation system coupled through electrical contacts to the electrode system for evaluating when the electrode system changes state;
- an electrically insulating and light transparent layer deposited on the print detector structure so as to cover at least a dominant portion of the print area, the electrode system, and the electrical contacts for selectively insulating the print forming element from the electrode system and the electrical contacts; and wherein the electrode system is made of a light transparent and electrically conductive material for allowing a print image to be captured of the print forming element on the at least one portion of the print area covered by the electrode system, and is configured for determining a dielectric constant of the print forming element.

8. The optical-electronic print recognizing device of claim 7, wherein the electrode comprises a plurality of interdigital electrodes covered by said insulating layer.

9. The detector as claimed in claim 7, wherein said electrode system simultaneously determines the dielectric constant of the print forming element while the print image of the print forming element is captured.

10. An optical-electronic print recognizing device for capturing print images of a print forming element comprising:

a print detector structure made of an electrically insulating and light transparent material and defining a print area for receiving a print forming element;

an electrode system coupled to said print detector structure for generating a change in state when the print forming element is proximate to at least one portion of the print area covered by the electrode system;

an electrical evaluation system coupled through electrical contacts to the electrode system for evaluating when the electrode system changes state;

an electrically insulating and light transparent layer deposited on the print detector structure so as to cover at least a dominant portion of the print area, the electrode system, and the electrical contacts for selectively insulating the print forming element from the electrode system and the electrical contacts;

wherein the electrode system is made of a light transparent and electrically conductive material for allowing a print image to be captured of the print forming element on the at least one portion of the print area covered by the electrode system, is configured for determining an electrical impedance of the print forming element, and further comprises at least one double dot electrode and at least one lead out contact, and said electrically insulating layer covers the at least one lead out contact while leaving the double dot electrode uncovered.

11. The optical-electronic print recognizing device of claim 10, wherein the electrically insulating and light transparent layer defines a window for exposing the double dot electrode to the print forming element and allowing the print forming element to be in electrical contact with the double dot electrode when the print forming element is proximate to the print area.

12. An optical-electronic print recognizing device for capturing print images of a print forming element comprising:

a print detector structure made of an electrically insulating and light transparent material and defining a print area for receiving a print forming element;

an electrode system coupled to said print detector structure for generating a change in state when the print forming element is proximate to at least one portion of the print area covered by the electrode system;

an electrical evaluation system coupled through electrical contacts to the electrode system for evaluating when the electrode system changes state;

an electrically insulating and light transparent layer deposited on the print detector structure so as to cover at least a dominant portion of the print area, the electrode system, and the electrical contacts for selectively insulating the print forming element from the electrode system and the electrical contacts; and wherein the electrode system is made of a light transparent and electrically conductive wire for allowing a print image to be captured of the print forming element on the at least one portion of the print area covered by the electrode system, and the electrically conductive wire comprises a glass fiber doped by metal ions.

13. An optical-electronic print recognizing device for capturing print images of a print forming element comprising:

a print detector structure made of an electrically insulating and light transparent material and defining a print area for receiving a print forming element;

an electrode system coupled to said print detector structure for generating a change in state when the print forming element is proximate to at least one portion of the print area covered by the electrode system;

an electrical evaluation system coupled through electrical contacts to the electrode system for evaluating when the electrode system changes state;

an electrically insulating and light transparent layer deposited on the print detector structure so as to cover at least a dominant portion of the print area, the electrode system, and the electrical contacts for selectively insulating the print forming element from the electrode system and the electrical contacts; and wherein the electrode system is made of a light transparent and electrically conductive material for allowing a print image to be captured of the print forming element on the at least one portion of the print area covered by the electrode system, and the electrically insulating and light transparent layer completely covers the electrode system and allows the print forming element to be placed within an electric field generated by the electrode system when the print forming element is proximate to the print area.

* * * * *